United States Patent [19]

Draenert

[11] Patent Number: 4,966,601
[45] Date of Patent: Oct. 30, 1990

[54] EVACUATABLE BONE CEMENT SYRINGE

[76] Inventor: Klaus Draenert, Gabriel-Max-Str. 3, D-8000 Munich 90, Fed. Rep. of Germany

[21] Appl. No.: 464,563

[22] Filed: Jan. 16, 1990

Related U.S. Application Data

[63] Continuation of Ser. No. 388,745, Aug. 2, 1989, abandoned, which is a continuation of Ser. No. 131,135, filed as PCT DE87/00122 on Mar. 20, 1987, published as WO87/05491 on Sep. 24, 1987, abandoned.

[30] Foreign Application Priority Data

Mar. 21, 1986 [DE] Fed. Rep. of Germany ....... 3609672

[51] Int. Cl.$^5$ .................... A61M 5/245; A61F 5/04; B01D 39/00
[52] U.S. Cl. ........................ 606/92; 606/94; 604/232; 55/189; 55/193
[58] Field of Search ............ 128/83; 604/232; 606/86, 92, 93, 94; 55/36, 55, 189, 190, 193

[56] References Cited

U.S. PATENT DOCUMENTS

| | | | |
|---|---|---|---|
| 773,877 | 11/1904 | Lorillard | 55/189 X |
| 2,155,397 | 4/1939 | Brandon | 53/88 |
| 2,570,835 | 10/1951 | Mooney et al. | 55/189 X |
| 2,744,648 | 5/1956 | Scherr | 215/309 |
| 2,798,573 | 7/1957 | Vesterdal et al. | 55/155 |
| 3,085,039 | 4/1963 | Baum | 55/36 X |
| 3,795,245 | 3/1974 | Allen, Jr. et al. | 128/303.1 |
| 3,813,223 | 5/1974 | Fleck | 215/309 |
| 3,844,738 | 10/1974 | Reinhoudt et al. | 55/36 |
| 4,036,387 | 7/1977 | Feaster | 215/309 |
| 4,115,085 | 9/1978 | Barbe | 55/193 |
| 4,277,184 | 7/1981 | Solomon | 606/93 |
| 4,411,163 | 10/1983 | White | 215/309 |
| 4,472,141 | 9/1984 | Dragon | 604/232 X |
| 4,546,767 | 10/1985 | Smith | 128/92 VQ |
| 4,551,135 | 11/1985 | Gorman et al. | 128/92 VQ |
| 4,593,685 | 6/1986 | McKoy et al. | 606/92 X |
| 4,655,749 | 4/1987 | Fischione | 606/94 X |
| 4,671,263 | 6/1987 | Draenert | 128/92 V |
| 4,718,910 | 1/1988 | Draenert | 606/86 X |

FOREIGN PATENT DOCUMENTS 2814353 10/1978 Fed. Rep. of Germany ........ 128/92

Primary Examiner—Robert A. Hafer
Assistant Examiner—D. Neal Muir
Attorney, Agent, or Firm—Kinney & Lange

[57] ABSTRACT

The invention relates to an evacuatable bone cement syringe comprising a container (8) for receiving the bone cement prior to its application, and comprising a pressure generating apparatus for precompressing the bone cement in the container (8). A bell (100) comprising a vacuum tube (110) is placed over the container (8) and held in place by a flange (105) so that the gases which escape during the process of precompression can be sucked off. In this way it is possible to reduce the porosity of the bone cement which is being applied.

8 Claims, 2 Drawing Sheets

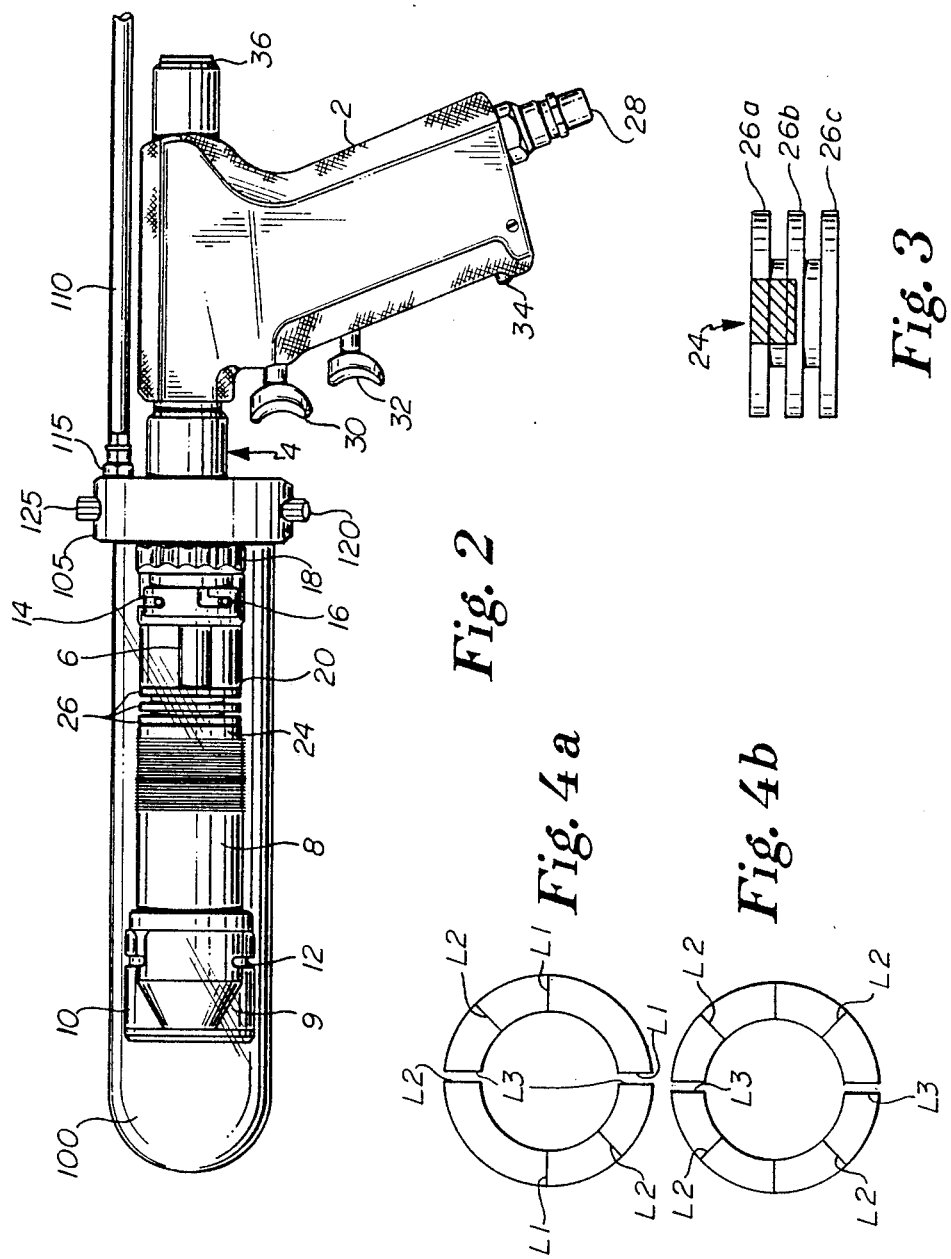

EVACUATABLE BONE CEMENT SYRINGE

This is a continuation of application Ser. No. 07/388,745 filed on Aug. 2, 1989, now abandoned, which is a continuation of application Ser. No. 07/131,135 filed as PCT DE87/00/22 on Mar. 20, 1987, published as WO87/05491 on Sept. 24, 1987, now abandoned.

BACKGROUND OF THE INVENTION

The invention relates to an apparatus and a process for mixing and applying bone cement. An apparatus of this kind is known, for instance, from EP-A1-170 120.

The components of artificial joints are usually anchored to the bony bed using cold polymerizing two-components resins called bone cement. The bone cement hardens as soon as it has been applied and achieves an anchoring of the prosthesis component into the bony bed by means of its plastic properties. Polymethylmethacrylates (PMMA) have been used for more than 20 years as bone cement; they comprise powdery bead polymers superficially dissolved in a liquid monomer and are finally embedded therein by polymerisation. In the mixing phase the monomer surrounds the pellet-shaped bead polymer. This first leads to a bloating of the pellets in which a considerable amount of air bubbles are trapped. The chemical reaction of the bone cement is initiated by a starter reaction, wherein dibenzoyl peroxide is usually activated by an activator, i.e. p-amino-toluidine, and then a radical chain polymerisation is initiated. This process of polymerisation takes place exothermically. In addition to the trapped air bubbles, when the polymer pellets are surrounded by the monomer, so-called "lee phenomena" appear regularly. Also, the monomer liquid evaporates during the process of exothermic polymerisation which leads to the fact that in the end the hardened polymer is riddled with various bubbles of different ethiology and genesis.

As a rule, the polymer powder or prepolymer is added to the monomer and mixed in a bowl using a spatula. In the processing phase which follows the mixing phase, the bone cement is applied to the bony bed, for instance to the femoral medullary canal or the bony acetabulum, both of which have been prepared for the anchoring of the cemented prosthesis components; the application is usually performed by hand and sometimes using a syringe. Such a syringe is described in DE-A-28 01 706 or in EP-A1-170 120, for instance. By using a bone cement syringe, markedly better results were achieved in the technique of cementing in view of the cement anchorage in bones than had been achieved with the conventional method in which the bone cement was finger packed.

On the one hand the aim of improving the cementing technique was to improve the anchorage in the bone by impacting the bone cement, on the other, however, one also wanted to solidify the bone cement itself and improve the material properties of the plastic mass. For this reason an attempt was made to compress the bone cement as described, for instance, in EP-A1-170 120. Other authors attempted to remove the air bubbles by evacuating them during the mixing phase as is done with cement used on building sites. However, as the evaporation temperature of the monomer reaches its critical stage at room temperature, monomer bubbles already formed in the bone cement at a pressure of under 400 mbar (40 kPa). This lead to the development of processes (LIDGREN, DRAR and MOELLER, "Polymethylmethacrylate Mixing with Special Reference to Strength", Acta Orthop Scand, 1984, LIDGREN, BODELIND and MOELLER, "Mechanical Properties of Bone Cement with Special Reference to Vacuum Mixing and Chilling", presented at the Swedish Medical Society's Meeting on 30th November 1984) which attempted to prevent the monomer from evaporating by supercooling it and achieved a major reduction in the number of bubbles in the bone cement paste. Due to the reduction of the temperature, however, the process of polymerisation took longer as the chemical reactions took place more slowly. What is more, problems arose from the complicated process of supercooling the monomer and the mixing vessel.

Summary of the Invention

The object of the invention is to avoid the above disadvantages when evacuating the bone cement and to provide an apparatus and a process for mixing and applying bone cement with which the pore volume enclosed in the bone cement can be diminished even further and the stability of the completely polymerised bone cement increased.

This object is achieved especially by the features of the patent claims.

The invention is based on the principle of evacuating the bone cement whilst mechanically pre-pressurizing it at the same time.

The use of the bone cement syringe according to EP-A1-170 120, in which the bone cement can be mechanically prepressurized by compressed air, is aimed at pushing out the bubbles between the lamellar cylinder and the cap. The bone cement itself cannot pass through the cap and the lamellar cylinder. If a suction bell is placed over the cartridge and a vacuum applied at the same time, no evaporation of the monomer can be observed during the precompression phase, it can far more be seen that the trapped bubbles can escape both through the cap and the lamellar cylinder depending on the intensity of the applied vacuum and the viscosity of the bone cement.

By pressurising the bone cement column in its applicator, the mechanical pressure applied to the cement mixture can affect the evaporation curve of the monomer in such a way that the non-vacuum-tight cap or the non-vacuum-tight lamellar cylinder will let the trapped air bubbles through if a vacuum is applied at the same time, whereas the bone cement itself remains firmly compressed.

The effect of the evacuation can be enhanced by radially notching the lamellae of the lamellar cylinder, e.g. with a scalpel, so that no slot defects occur and the lamellae can be moved in opposition to one another in the area of sectors either in an offset fashion or in a synchronous fashion. This process allows air bubbles and trapped gas bubbles to escape through the lamellar cylinder very easily, whereas the cement itself can only flow into the first or maybe just into the second groove of the tri-lamellar cylinder for instance, whereupon the lamellae become more stable. Only the trapped gas and the excess liquid monomer can flow past the metal plunger.

In order to control the pressure during the process of evacuation, one can preferably use a simple pressure measuring apparatus comprising a small cylinder having a flat coil, which cylinder has a coloured calibration arranged on its outer surface, for instance variously anodized aluminium rings, and which is sucked quite a way into the flange of the vacuum bell. Such an evacuating unit can be very easily equipped for controlled evacuation, too. It is, for instance, possible to apply a flange to the barrel of the bone cement pistol according to EP-A1-170 120 onto which a transparent plastic or glass bell comprising ground and polished flange stoppers can be mounted. The one side of the flange can be equipped with the pressure measuring cylinder described above. By means of a needle valve comprising a knurled screw on the opposite side, the intensity of the vacuum can be very easily regulated. The vacuum bell can be evacuated through a vacuum tube via a suction connection lying parallel to the handle of the bone cement pistol. The non-vacuum-tight closure cap of the cement vessel and the lamellae of the lamellar cylinder in the pressure piston, said lamellae having been specially prepared to this effect, let the gas bubbles pass. In this way it is possible to achieve a considerable reduction in the pore volume of the bone cement as soon as the preparation phase sets in. The evacuation is continued until the bone cement has been polymerised to such an extent that its solidification is apparent. This will take place between the first and the sixth minute depending on the temperature and viscosity of the bone cement being used. This is followed by releasing the vacuum and precompression, and once the cap has been removed, the cement is applied to the bony bed while still in its plastic phase. As described in EP-A1-170 120, any intensity of pressure can be used to carry out impaction. The vacuum bell and the material used for the adapter flange can be completely sterilised. One of the plastics which can be advantageously used for the vacuum bell is TPX ®.

Brief Description of the Drawings

In the following, the figures will be used to explain the invention in greater depth.

FIG. 2 shows the assembled bone cement pistol of the invention, FIG. 3 is a cross-section of a lamellar cylinder comprising three lamellae, and FIG. 4a and 4b both show a top view of various embodiments of a lamella.

Description of the Preferred Embodiment

Figure 1:
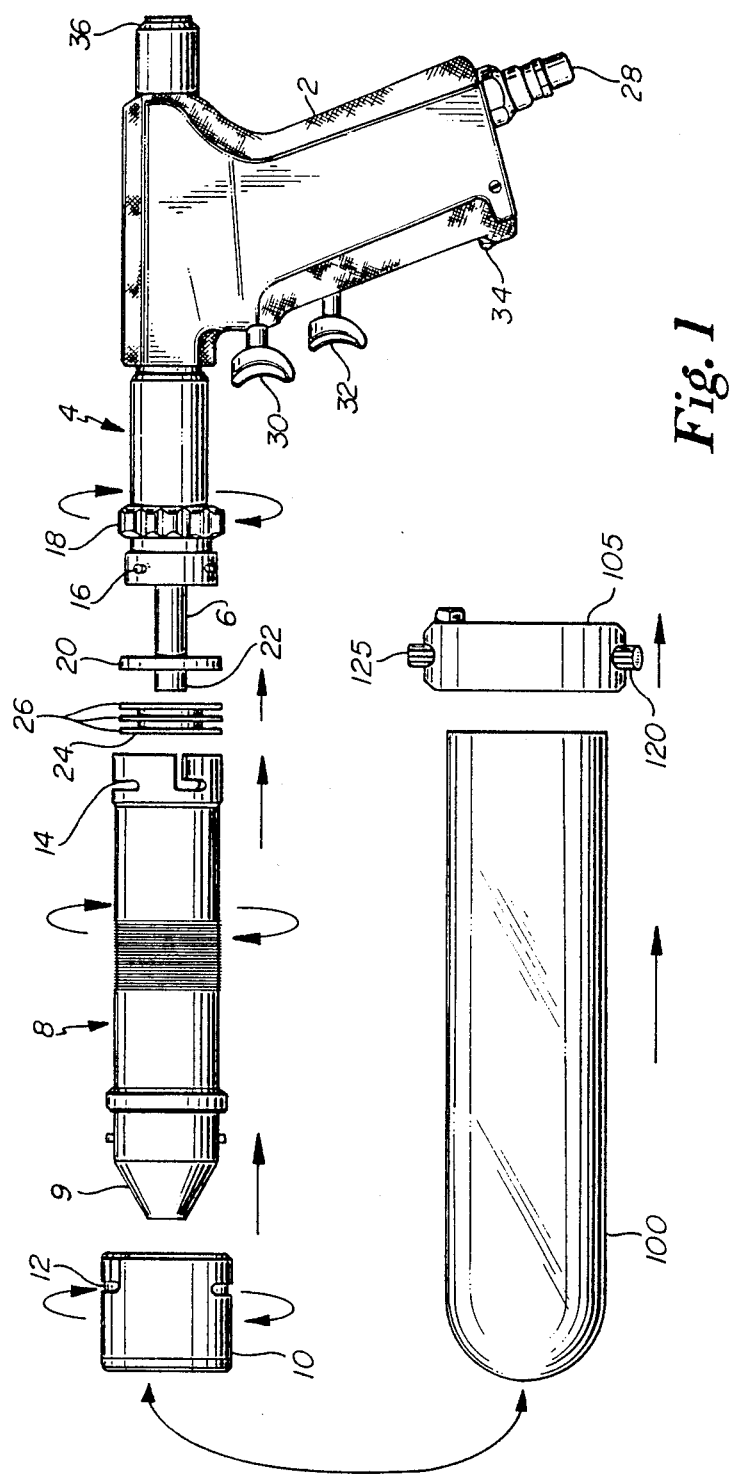
FIG. 1 is an view of the individual components of the dismantled bone cement pistol of the invention.

The basic structure and the mode of operation of a bone cement pistol which essentially corresponds to the bone cement pistol of the invention, but does not include the evacuation of the bone cement is described in EP-A1-170 120.

The bone cement pistol has a handle 2, a casing 4, ejector means 6, a bone cement container 8 with a conically tapered front part 9 and a closure cap 10. The container 8 and the closure cap 10 are connected by a bayonet closure 12. Furthermore, the casing 4 is provided with a snap closure (quick closure) 14 and pins 16 with which the container 8 is connected to the casing 4, which snap closure also comprises a rotatable safety mechanism for the bayonet closure 12. Furthermore there is provided a slider 20 having one projection 22, a lamellar cylinder or lamellar member 24 having three flexible lamellae 26, a compressed air connection 28 to be connected to a pressurised air source (not shown), a pressure inlet valve 30 in the shape of a dosing valve, an unlocking valve 32 for unlocking the pressure inlet valve 30, a vent button 34 and a pressure display 36.

The bone cement pistol of the invention also comprises a vacuum bell or suction bell 100, a flange 105 which connects the bell 100 to the casing 4 of the bone cement pistol and a vacuum tube 110 the one end of which is connected by connections 115 to the flange 105 and the other end of which is connected to a pump (not illustrated). The flange 105 comprises a pressure measuring apparatus 120 and an adjustable valve 125.

The mode of operation of the bone cement pistol is described above. During the precompression phase, in which the lamellar member 24 is pressed against the cement in the container 8, the air is sucked out of the bell 100 via the vacuum tube 110. Whereas the bone cement cannot pass through the cap 10 or the lamellar member 24 and remains firmly enclosed, the bubbles trapped in the bone cement are pressed out of the same by the pressure exerted by the lamellar member 24. They can escape via both the (non-air-tight) cap 10 and the lamellae 26 of the lamellar member 24 which do not fit with the container 8 in an air-tight fashion. As the bone cement is subjected to pressure, no monomer can evaporate during this process.

The lamellar member 24 and its three lamellae 26a, 26b and 26c illustrated in FIG. 3 are preferably shaped in such a manner that the lamella 26c facing the bone cement has the smallest diameter and the lamellae 26b and 26a both have a slightly larger diameter. Lamella 26c, for instance, has a diameter of 25.78 mm, lamella 26b has a diameter of 25.80 mm and lamella 26a has a diameter of 25.82 mm. In this way it is possible to compensate for process tolerances and to ensure that when pressurized, the bone cement can pass through the first or second lamella at the most, but not through all three lamellae 26 of the lamellar member 24.

The lamellae illustrated in FIG. 4 preferably exhibit radial slots. In FIG. 4, L1 are the slots of the first lamella which faces the bone cement, L2 are the slots of the second lamella and L3 are the slots of the third lamella. In the two embodiments according to FIG. 4a and 4b, each of the slots of the individual lamellae are radially offset. When the lamellar member is pressurized and pressed against the enclosed bone cement, the lamellae may slightly deform, but finally become stable enough to prevent the bone cement from passing through all three lamellae. It is quite possible to provide more than three lamellae for this purpose.

I claim:

1. An apparatus for mixing and applying bone cement, comprising:
   (a) a container for receiving the bone cement prior to its application,
   (b) a pressure generating apparatus operative within the container for prepressurizing the bone cement wherein the container and for later applying the bone cement,
   (c) vent means in gaseous communication with the bone cement for enabling gases in the bone cement to escape out of the bone cement and the container when pressure is exerted by the pressure generating apparatus,
   (d) evacuating means in gaseous communication with the container for sucking off the gases which escape under pressure from the container,
   (e) means for retaining the bone cement in the container which will permit escape of gases while the cement is pre-pressurized.

2. An apparatus according to claim 1 wherein the evacuating means comprises a bell placed over the container.

3. An apparatus according to claim 2 and further including a casing and wherein the bell is connected to the casing by means of a flange.

4. An apparatus according to claim 3, wherein the flange comprises a connection for a vacuum tube.

5. The apparatus according to claim 4 further comprising means for measuring and controlling the pressure in the bell.

6. The apparatus according to claim 5 wherein the pressure generating apparatus comprises an ejector means having a lamellar member at its forward end, the lamellar member comprising at least three lamellae for pushing out the cement, each lamella having a slightly different diameter.

7. The apparatus according to claim 6, wherein the lamellae have radial slots, the slots of each lamella preferably being offset.

8. An apparatus for mixing and applying bone cement, comprising:

a container for receiving the bone cement prior to its application;

a pressure generating apparatus comprising an ejector means fitting cementtight in said container and being movable within said container for prepressurizing the bone cement within the container and for later applying the bone cement, vent means in gaseous communication with the bone cement for enabling air bubbles and other gases to escape out of the bone cement and out of the container when pressure is exerted onto the bone cement by means of the ejector means; and evacuating means in gaseous communication with the container, said evacuating means comprising suction bell means placed over the container and means for evacuating the space within said suction bell means including the space around the container so that the air and other gases which escape from the bone cement and the container are drawn off while the bone cement is pre-pressurized, means for retaining the bone cement in the container which will permit escape of gasses while the bone cement is pre-pressurized.

* * * * *

UNITED STATES PATENT AND TRADEMARK OFFICE
CERTIFICATE OF CORRECTION

PATENT NO. : 4,966,601
DATED : October 30, 1990
INVENTOR(S) : Klaus Draenert

It is certified that error appears in the above-identified patent and that said Letters Patent is hereby corrected as shown below:

Col. 4, line 53, delete "prepressurizing", insert --pre-pressurizing--.

Col. 4, line 54, delete "wherein", insert --within--.

Col. 6, line 22, delete "gasses", insert --gases--.

Col. 6, line 12, delete "and".

Col. 6, line 20, delete "pre-pressurized,", insert--pre-pressurized; and--.

Signed and Sealed this

Fifth Day of May, 1992

*Attest:*

DOUGLAS B. COMER

*Attesting Officer*   *Acting Commissioner of Patents and Trademarks*